(12) United States Patent
Piontkowski

(10) Patent No.: US 7,207,531 B2
(45) Date of Patent: Apr. 24, 2007

(54) HEAD MANIPULABLE BINOCULAR MICROSCOPE SUPPORT

(76) Inventor: Paul K. Piontkowski, 2310 Popkins La., Alexandria, VA (US) 22306

( * ) Notice: Subject to any disclaimer, the term of this patent is extended or adjusted under 35 U.S.C. 154(b) by 114 days.

(21) Appl. No.: 10/320,385

(22) Filed: Dec. 17, 2002

(65) Prior Publication Data

US 2004/0113029 A1  Jun. 17, 2004

(51) Int. Cl.
*A47F 5/00* (2006.01)
(52) U.S. Cl. .............................. 248/122.1; 248/125.9; 248/282.1; 359/409
(58) Field of Classification Search ............ 248/122.1, 248/123.11, 125.8, 125.9, 276.1, 278.1, 282.1, 248/288.31, 123.2, 364, 279.1, 280.11, 281.1, 248/283.1, 284.1, 324, 325; 359/409; 351/245; 403/56, 76, 122; 600/102, 228, 229, 249, 600/111
See application file for complete search history.

(56) References Cited

U.S. PATENT DOCUMENTS

| | | | | |
|---|---|---|---|---|
| 941,591 | A * | 11/1909 | Sweet ........................ | 248/282.1 |
| 2,479,720 | A * | 8/1949 | Brandt ....................... | 248/123.2 |
| 3,090,045 | A | 5/1963 | Hurst | |
| 3,290,985 | A * | 12/1966 | Bains et al. ................. | 359/896 |
| 3,434,772 | A | 3/1969 | Fogle | |
| 3,796,220 | A | 3/1974 | Bredemeier | |
| 3,830,230 | A * | 8/1974 | Chester ....................... | 600/249 |
| 4,170,336 | A * | 10/1979 | Malis ........................ | 248/279.1 |
| 4,175,826 | A | 11/1979 | Blaha et al. | |
| 4,344,595 | A * | 8/1982 | Heller et al. ................. | 248/542 |
| 4,364,629 | A | 12/1982 | Lang et al. | |
| 4,396,260 | A | 8/1983 | Takizawa et al. | |
| 4,411,627 | A * | 10/1983 | Breglia et al. ................ | 434/44 |
| 4,515,333 | A * | 5/1985 | Pugh et al. .................. | 248/123.11 |
| 4,518,231 | A | 5/1985 | Muchel et al. | |
| 4,592,096 | A * | 6/1986 | Glasheen ..................... | 2/427 |

(Continued)

FOREIGN PATENT DOCUMENTS

GB    2053502 A  *  2/1981

(Continued)

OTHER PUBLICATIONS

Prior Art—Advertisement—Varioscope M5 by Life Optics.

(Continued)

*Primary Examiner*—Korie Chan
(74) *Attorney, Agent, or Firm*—Dority & Manning

(57) ABSTRACT

A support for a medical instrument such as a binocular microscope including a plurality of piviotally connected arms connected to a wall, ceiling or vertical support mount. One of said arms being vertical and having ball joints at opposite ends, one connected to an adjacent arm and the other connected to the binocular microscope. An extension connected at one end to the binocular microscope and at an opposite end to a head harness for attaching to the head of an operator. Two of the arms are connected by a bearing having a vertical extension. One of the arms is pivotally connected to the vertical extension. A compressed gas cylinder is connected at one end to the vertical extension and at another end to the arm connected to the vertical extension. The arrangement is so that the operator can position the binocular microscope without use of any hands and with negligible resistance.

23 Claims, 3 Drawing Sheets

U.S. PATENT DOCUMENTS

| | | | |
|---|---|---|---|
| 4,594,608 A | 6/1986 | Hatae et al. | |
| 4,614,411 A | 9/1986 | Horenz | |
| 4,616,257 A * | 10/1986 | Kloots et al. | 348/370 |
| 4,657,356 A | 4/1987 | Matsumura | |
| 4,787,734 A | 11/1988 | Matsumura | |
| 4,849,778 A * | 7/1989 | Samuelson | 396/428 |
| 4,895,328 A * | 1/1990 | Ryan | 248/124.1 |
| 5,213,293 A * | 5/1993 | Muentener et al. | 248/123.11 |
| 5,252,070 A * | 10/1993 | Jarrett | 434/59 |
| 5,253,832 A * | 10/1993 | Bolas et al. | 248/123.11 |
| 5,257,998 A * | 11/1993 | Ota et al. | 606/130 |
| 5,365,607 A | 11/1994 | Benevento, Jr. et al. | |
| 5,420,716 A * | 5/1995 | Fukaya | 359/368 |
| 5,537,248 A | 7/1996 | Sander | |
| 5,642,220 A * | 6/1997 | Kleinberg et al. | 359/384 |
| 5,667,186 A * | 9/1997 | Luber et al. | 248/550 |
| 5,748,366 A * | 5/1998 | Yasunaga et al. | 359/368 |
| 5,841,509 A | 11/1998 | Harooni et al. | |
| 5,913,412 A | 6/1999 | Huber et al. | |
| 6,081,372 A | 6/2000 | Mura | |
| 6,147,800 A | 11/2000 | Faber | |
| 6,290,368 B1 | 9/2001 | Lehrer | |
| 6,471,165 B2 * | 10/2002 | Twisselmann | 248/123.11 |
| 6,543,914 B2 * | 4/2003 | Sander | 362/401 |
| 6,606,192 B2 * | 8/2003 | Haran | 359/409 |
| 6,763,286 B2 | 7/2004 | Metelski | |
| 6,859,312 B1 | 2/2005 | Atchison | |

FOREIGN PATENT DOCUMENTS

| | | | |
|---|---|---|---|
| JP | 07184926 A * | 7/1995 | |
| WO | 9203756 | 5/1992 | |
| WO | 9609566 | 3/1996 | |
| WO | 0055673 A1 | 9/2000 | |
| WO | 0138919 A1 | 5/2001 | |
| WO | 03069214 | 8/2003 | |

OTHER PUBLICATIONS

Prior Art—Advertisement—Varioscope AF3 by Life Optics.
Prior Art—Advertisement—Seiler Instrument Microscope Division—Model SSI-202 Dental Microscope.

* cited by examiner

HEAD MANIPULABLE BINOCULAR MICROSCOPE SUPPORT

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

Surgical and analytical microscopes have been supported in the past usually by a system of rather heavy arms attached to a support of some type at one end and at an opposite end to the microscope. The microscope is usually positioned by a clinitian grasping the microscope with both hands each time it had to be relocated during a surgical or analytical procedure. The microscope usually weights somewhere between ten and more pounds and the support arms are each relatively heavy. Thus, it requires some effort on the part of the clinitian to accurately position the microscope due to frictional resistance between the movable parts. Also, the clinitian has to give up use of both hands while moving the microscope during the surgical or analytical procedure.

BRIEF SUMMARY OF THE INVENTION

The invention pertains to a support system comprising a plurality of support arms pivotally connected together to support a binocular microscope at one end of the arms and connected to a suitable mount at the opposite end of the arms. A head harness is connected to the microscope so that a clinitian can manipulate the microscope by his head into a desired position during a surgical or analytical procedure with both hands free.

DETAILED DESCRIPTION OF THE INVENTION

While this invention is primarily a support and guidance system for a binocular microscope during a surgical or analytical procedure, it may also be used for supporting and guiding a laser (see U.S. Pat. No. 3,796,220) or other medical instruments in a surgical or analytical procedure that requires following the line of sight of the clinician.

Figure 1:
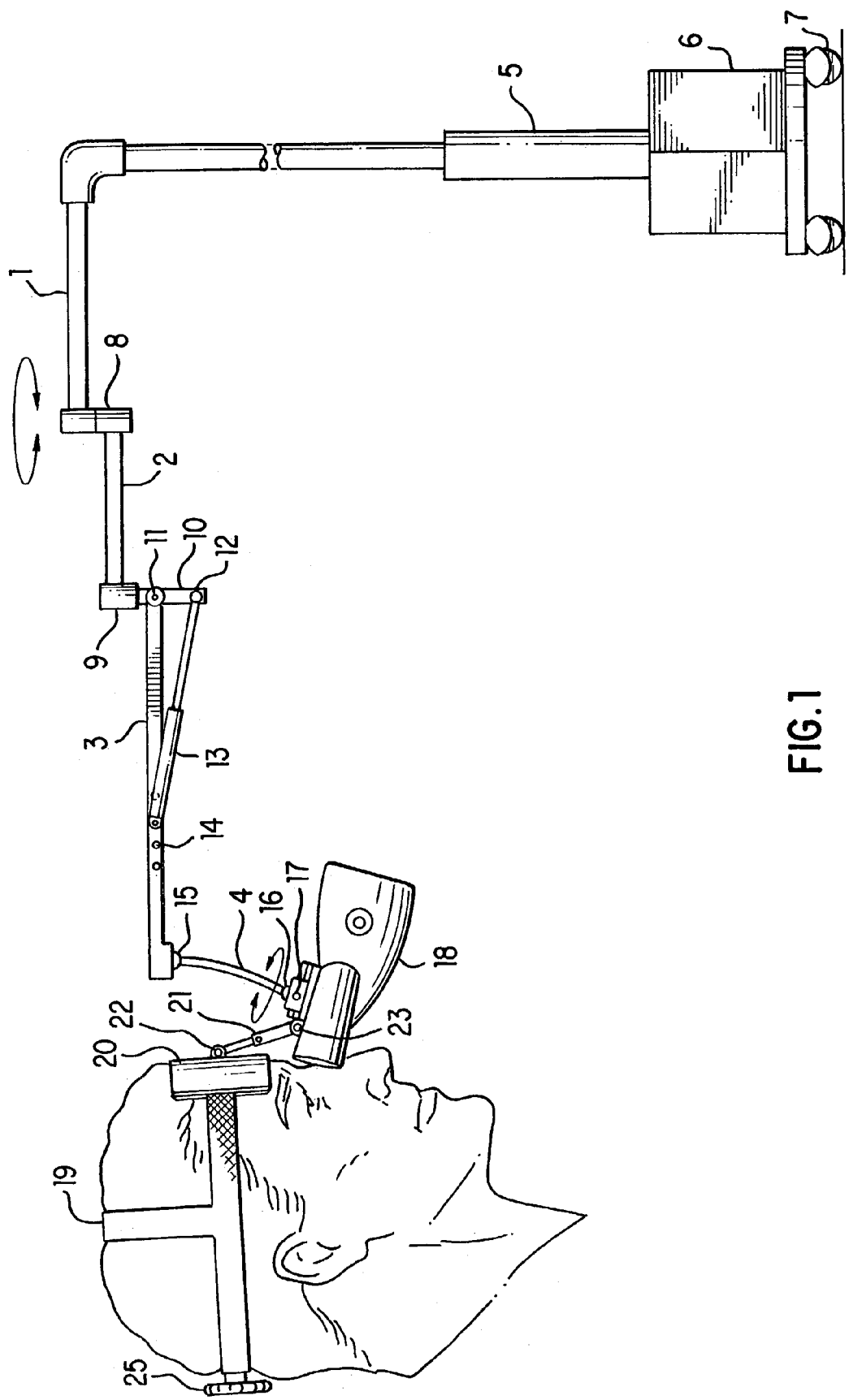
FIG. 1 shows a side view of the entire assembly of elements as used.
Figure 2:
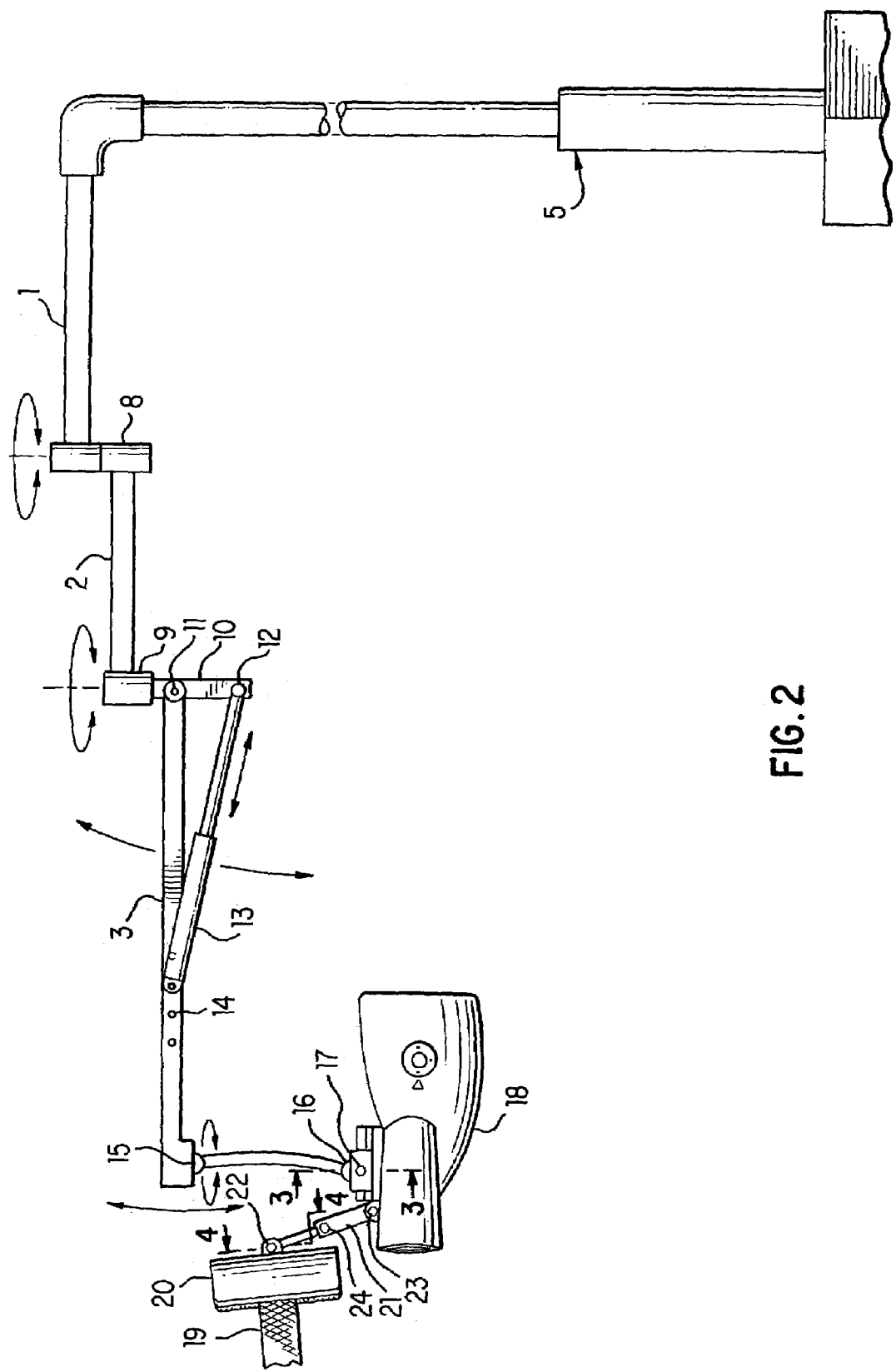
FIG. 2 is an enlarged view of the assembly of FIG. 1.

A mount for the apparatus may include any number of conventional systems for raising and lowering the apparatus. In the instant invention, the mount as illustrated in FIG. 1 includes a housing 6 mounted on wheels 7 and a telescoping device 5. The telescoping device may be raised or lowered by means of a rack and pinion, motorized screw or hydraulic piston and cylinder for example. The apparatus may also be supported by attaching an arm of the apparatus to a wall or ceiling mount or to an adjustable in length mount connected to a dental chair accessory pole.

Figure 3:
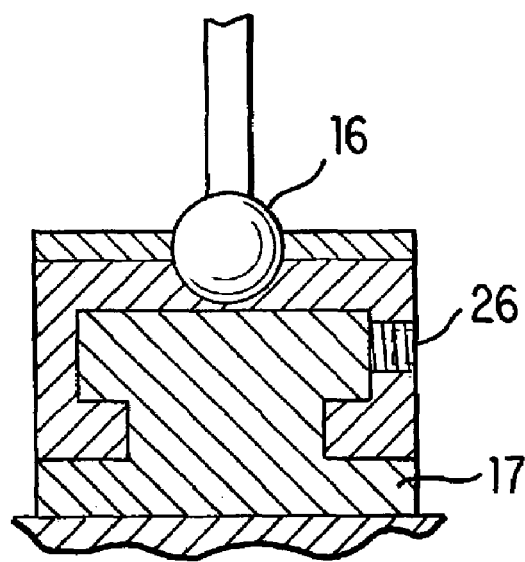
FIG. 3 is a sectional view taken along the lines 3—3 in FIG. 2.
Figure 4:
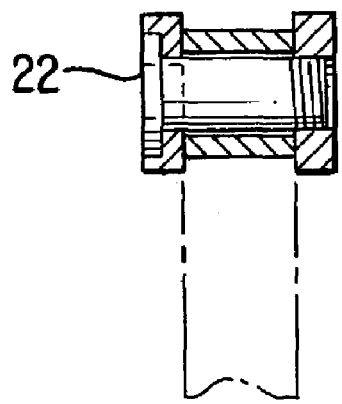
FIG. 4 is a sectional view taken along the lines 4—4 in FIG. 2.

A system of arms connects a binocular microscope 18 to the telescoping portion 5 of the mount. A first arm 1 is connected to the telescoping portion 5 at one end and to a second arm 2 at the other end by a bearing 8. The second arm 2 is connected to a third arm 3 by means of a bearing 9 including a vertical extension 10. The third arm is pivotally connected to the vertical extension at 11. A compressed gas spring 13 is pivotally connected at one end to the vertical extension 10 at 12 and at an opposite end to the third arm 3. The compressed gas spring applies a counterbalancing force which is required for the setting of an equilibrium condition upon alteration of the third arm in a vertical direction. The third arm 3 has a plurality of perforations such as 14 wherein the attached location of the compressed gas spring can be varied to adjust the force applied by the compressed gas spring against the arm 3. A forth arm 4 is attached to the third arm 3 at one end by a ball joint 15 and at the opposite end to the binocular microscope 18 by another ball joint 16. The ball joint 16 includes a combination cage and slide 17 as best seen in FIG. 3, attached to the binocular microscope 18. The cage can move on the slide to help balance the microscope and can be held in place by a locking screw 26. Arm 2 can rotate 360 degrees at bearing 8, arm 3 can rotate 360 degrees at bearing 9 and arm 4 can rotate 360 degrees at both ball joints 15 and 16. The arm 4 can pivot at ball joints 15 and 16 in any direction.

An extension means 21 includes splined or noncircular in cross-section telescoping members which may be adjusted in length and locked in position by a setscrew 24. The extension means 21 is pivotally connected to both the binocular microscope and to a head harness so that it can be adjusted relative to the head harness and binocular microscope and held in position by lock screws 22 and 23. The head harness includes a padded member 20 and straps 19 attached about a clinician's head. The straps may be tightened by a belt-buckle arrangement, VELCRO members, a knob type tightener as shown at 25 or other conventional means.

Other arm means could be substituted for the arms 1, 2 and 3 as illustrated. For example, a telescoping arrangement of arms could be pivotally attached to a suitable mount at one end and at an opposite end to a vertical arm having ball joints at opposite ends such as disclosed herein for the arm 4 to support the microscope, or the microscope could be attached directly to the end of the telescoping arms. The number of attached arms could be increased or decreased as desired without departing from the scope of the invention. Further, a cable could be attached at one end to a microscope and at an opposite end to an adjustable mount.

With the system as described above, the clinician can position the binocular microscope very smoothly and precisely with the head and with minimum resistance, allowing both hands to be free for any use necessary in the surgical or analytical procedure.

What is claimed is:

1. A medical instrument support comprising: a wall, ceiling or vertical support mount, an adjustable arm attached at one end to said support mount and at an opposite end to a medical instrument for supporting and positioning said medical instrument, an attachment connecting said medical instrument to the head of an operator for positioning of the medical instrument by the head of the operator, said adjustable arm includes a first arm pivotally connected to a second arm by a first bearing and a third arm pivotally connected to said second arm by a second bearing, said adjustable arm includes a vertically extending arm portion connected at one end to said third arm and at an opposite end to said medical instrument, said one end of said vertically extending arm portion includes a first ball joint connecting said third arm to said vertically extending arm portion, said medical instrument being connected to said vertically extending arm portion at said opposite end by a second ball joint.

2. The support as defined in claim 1, wherein said second ball joint connecting said vertically extending arm portion to said medical instrument includes a cage mounted on a slide and a locking screw for adjustably locking said cage on said slide.

3. The support as defined in claim 1, wherein said second bearing for connecting said second arm to said third arm includes a vertical extension, said third arm being pivotally attached about a horizontal axis to said vertical extension, a compressed gas spring pivotally attached at one end to said vertical extension about a horizontal axis and at another end to an end portion of said third arm to apply a counterbalancing force which is required for the setting of an equilibrium condition upon alteration of the third arm in a vertical direction.

4. The support as defined in claim 1, wherein said attachment connecting said medical instrument to the head of an operator includes an adjustable head harness connected to said medical instrument by an extension.

5. The support as defined in claim 4, wherein said extension has a pivotal connection including a set screw at opposite ends for connecting said extension to said adjustable head harness and said medical instrument.

6. The support as defined in claim 4, wherein said adjustable head harness includes a padded surface for engaging the forehead of an operator.

7. The support as defined in claim 1 wherein said medical instrument is a binocular microscope.

8. The support as defined in claim 1, wherein said mount includes means for vertically adjusting the height of said adjustable arm.

9. A binocular microscope comprising: a wall, ceiling or vertical support mount; a binocular microscope, a series of arms connecting said mount to said binocular microscope, said series of arms including a first arm, a second arm being pivotally connected to said first arm by a first bearing and a third arm being pivotally connected to said second arm by a second bearing, a vertical arm pivotally connected at one end to said third arm and at an opposite end to said binocular microscope, an adjustable head harness, for attaching to the head of an operator, connected to said binocular microscope by an extension, said second bearing for connecting said third arm to said second arm includes a vertical extension, said third arm being pivotally attached to said vertical extension to pivot about a horizontal axis, a compressed gas spring pivotally attached at one end to said vertical extension to pivot about a horizontal axis and pivotally attached at another end to an end portion of said third arm to apply a counterbalancing force which is required for the setting of an equilibrium condition upon alteration of the third arm in a vertical direction.

10. The support as defined in claim 9, wherein said first, second and third arms are positioned so that said second arm can rotate 360 degrees about said first bearing connecting said second arm with said first arm and said third arm can rotate 360 degrees about said second bearing connecting said second arm with said third arm.

11. The support as defined in claim 9, wherein said vertical arm is connected at one end to said binocular microscope by a first ball joint and at an opposite end to said third arm by a second ball joint.

12. The support as defined in claim 11, wherein said first ball joint includes a cage mounted on a slide and a locking screw for adjustably locking said cage on said slide.

13. The support as defined in claim 9, wherein said extension for connecting said adjustable head harness to said binocular microscope has a pivotal connection including a set screw at opposite ends.

14. The support as defined in claim 9, wherein said extension includes telescoping members and a set screw for adjusting and locking said telescoping members in position.

15. The support as defined in claim 9, wherein said mount includes means for vertically adjusting the height of said series of arms.

16. A binocular microscope support including: a wall, ceiling or vertical support mount, a first arm connected to said mount, a second arm pivotally connected to said first arm by a first bearing, a third arm pivotally connected to said second arm by a second bearing having a vertical extension, said third arm being pivotally attached to said vertical extension about a horizontal axis, a compressed gas spring pivotally attached at one end to said vertical extension to pivot about a horizontal axis and pivotally attached at another end to an end portion of said third arm to apply a counterbalancing force which is required for the setting of an equilibrium condition upon alteration of the third arm in a vertical direction, a vertical arm connected at one end to a binocular microscope by a first ball joint and at another end to said third arm by a second ball joint, an extension connected at one end to said binocular microscope and at an opposite end to a head harness for attachment to the head of an operator.

17. A microscope system, comprising:
    an adjustable arm attached at one end to a support mount;
    a microscope assembly supported from said adjustable arm, said microscope assembly further comprising a head harness and a microscope adjustably connected to said harness so as to be disposed along an operator's line of sight upon the operator donning said head harness;
    said microscope assembly being variably positionable relative to said adjustable arm; and
    a weight counterbalancing device operably configured on said adjustable arm to compensate for weight of said microscope assembly supported by said adjustable arm, said weight counterbalancing device providing a counter balancing force such that the position and angular orientation of said microscope assembly is slaved to movement of the operator's head;
    a support member extending vertically between said microscope assembly and said adjustable arm, said microscope assembly supported below an end of said vertical support member;
    a universal joint connection between said vertical support member and said microscope assembly such that said microscope assembly has universal movement relative to said vertical support member; and
    a universal joint connection between said vertical support member and said adjustable arm such that said vertical support member has universal movement relative to said adjustable arm.

18. The microscope system as in claim 17, wherein said vertically extending support member is a generally rigid member connected at opposite ends thereof for universal movement relative to said microscope assembly and said adjustable arm respectively.

19. The microscope system as in claim 18, further comprising first and second ball joints connecting opposite ends of said vertically extending support member to said adjustable arm and said microscope assembly, respectively.

20. The microscope system as in claim 17, wherein said vertically extending support member is a cable member.

21. The microscope system as in claim 17, wherein said adjustable arm extends in a generally horizontal direction and is connected to said support mount at a first end, said microscope assembly supported from a second generally opposite end of said adjustable arm, and said weight counterbalancing device is mounted on said adjustable arm between said first and second ends.

22. The microscope system as in claim 21, wherein said adjustable arm comprises a plurality of adjustably connected arm segments, said weight counterbalancing device connected between a vertically adjustable said arm segment and a vertically non-adjustable said arm segment.

23. The microscope system as in claim 22, wherein said weight counterbalancing device comprises a gas spring.

* * * * *